(12) United States Patent
Urrusti et al.

(10) Patent No.: US 6,508,989 B1
(45) Date of Patent: Jan. 21, 2003

(54) AIR STERILIZATION SYSTEM FOR CHILD INCUBATORS

(75) Inventors: José Luis Urrusti; Carlos Aguilar Chávez, both of Colonia Villa Coyoacan (MX)

(73) Assignee: Arroba Ingenieria, Sa. De Cv., Ampliacion Asturias (MX)

( * ) Notice: Subject to any disclaimer, the term of this patent is extended or adjusted under 35 U.S.C. 154(b) by 0 days.

(21) Appl. No.: 09/370,534

(22) Filed: Aug. 9, 1999

(30) Foreign Application Priority Data

Aug. 10, 1998 (MX) .............................................. 9806424

(51) Int. Cl.$^7$ ................................................. A62B 7/08
(52) U.S. Cl. ........................ 422/121; 422/120; 422/121; 422/123; 422/124; 422/125; 422/186.3; 600/22
(58) Field of Search ................................ 422/120, 121, 422/123, 124, 125, 186.3; 600/22

(56) References Cited

U.S. PATENT DOCUMENTS

| | | | | |
|---|---|---|---|---|
| 3,789,853 A | * | 2/1974 | Reinhard | 600/22 |
| 3,809,065 A | * | 5/1974 | Gatts | 600/22 |
| 4,328,793 A | * | 5/1982 | Martin | 600/22 |
| 5,545,335 A | * | 8/1996 | Sween et al. | 422/186.3 |

* cited by examiner

Primary Examiner—Robert J. Warden, Sr.
Assistant Examiner—Imad Soubra
(74) Attorney, Agent, or Firm—Darby & Darby

(57) ABSTRACT

This Invention Patent refers to an air sterilization system for child incubators. The object of this Patent is to provide the child with air which is less polluted or free from pathogenic microorganisms that might put its health at risk or prolong its stay in the incubator and/or clinic or hospital, and that of the other persons or patients that might come into contact with the air exiting the same incubator in the case of a child with an infectious manifestations.

11 Claims, 3 Drawing Sheets

AIR STERILIZATION SYSTEM FOR CHILD INCUBATORS

BACKGROUND AND SUMMARY OF THE INVENTION

At present, child incubators consist of a compartment where the child is kept and an air conditioning compartment.

In general, there is a tray with perforations arranged for the circulation of air that separates the two compartments. Most of the incubator's air circulates between both compartments with the aid of a fan element that forces its flow; only a small portion of the flow is taken from outside the incubator, that is, fresh air from the atmosphere.

In most incubators, this fresh air passes through a filter that must retain particles greater than 0.5 microns, which may be inorganic, organic or even germs. However, fresh air that is possibly polluted may also enter the incubator when the hood that delimits the child's compartment or any of its doors or openings for the inclusion of lines, tubes or cables, are opened. In other incubators, the air filter is located in the air conditioning compartment, with the purpose of filtering the circulating air as well as the fresh air. Consequently, whether the incubator is of the type that only filters fresh air or the type that filters the circulating air, the air filter does not guarantee the retention of pathogenic germs any smaller than the pore of this same filter, such as diverse virus, spores and small bacteria. Due to the favorable temperature conditions, humidity and oxygen in the incubator and its circulating air, such pathogenic germs can proliferate, especially if the child remains for prolonged periods in the incubator and/or if there is not adequate and continuous cleaning and disinfection of the same incubator or else if the corresponding air filter is not changed often enough. Furthermore, a child that develops an infectious process and which abandons one incubator may infect another that was previously free from infections, if the child is introduced to such incubator and if the incubator is not rigorously disinfected. When this happens it is known as cross infection. It is also known that hospital infections, i.e. those acquired during one's stay in a clinic or hospital, are particularly difficult to combat due to the resistance acquired by the microorganisms against the disinfection agents used and the antibiotics administered to the patients. Furthermore, both full-term and premature new born babies, particularly the latter, are more vulnerable to infections than those of a greater age.

It is known that the lethal action of irradiation on microorganisms is due to the fact that such energy, on penetrating the material, acts on the SEEREPM (Space-Energetics Representation of Electronic Probablistic Manifestations) electronic orbitals that constitute atoms. When this alteration occurs in the molecular environment of microorganisms, their metabolic characteristics are altered. If the irradiation substantially alters the nucleonic acids (basically the RNA and DNA) of the microorganism, its essential metabolism is severely disabled and it dies.

With the aim of providing circulating air which is practically sterile and free of pathogenic microorganisms for the child occupying the incubator, the system covered by the invention, incorporates a non-ionizing source of radiation, which we hereinafter call irradiation, and which is effective in the annihilation of such pathogenic agents with sufficient doses. The source of irradiation is located close to or adjacent to the air conditioning compartment, specifically in a part hereinafter called the irradiation chamber. The circulating air is forced to pass through a region irradiated by the mentioned source, this region hereinafter being called the "sterilization zone". The irradiation chamber can be physically separated from the sterilization zone by a means that allows the passage of the irradiation from its source to the sterilization zone. This sterilization zone does not have any physically separation from the air circulating in the air conditioning compartment. Therefore, the irradiation energy from the sterilization system acts on the circulating air and is independent from the air filter which may or may not exist in the incubator.

BASIC DESCRIPTION OF THE INVENTION

The characteristic details of this air sterilization system for child incubators are listed in the following description and in the illustration thereof. The reference signs to indicate the parts and the figures shown are the same.

DETAILED DESCRIPTION OF THE INVENTION

Figure 1:
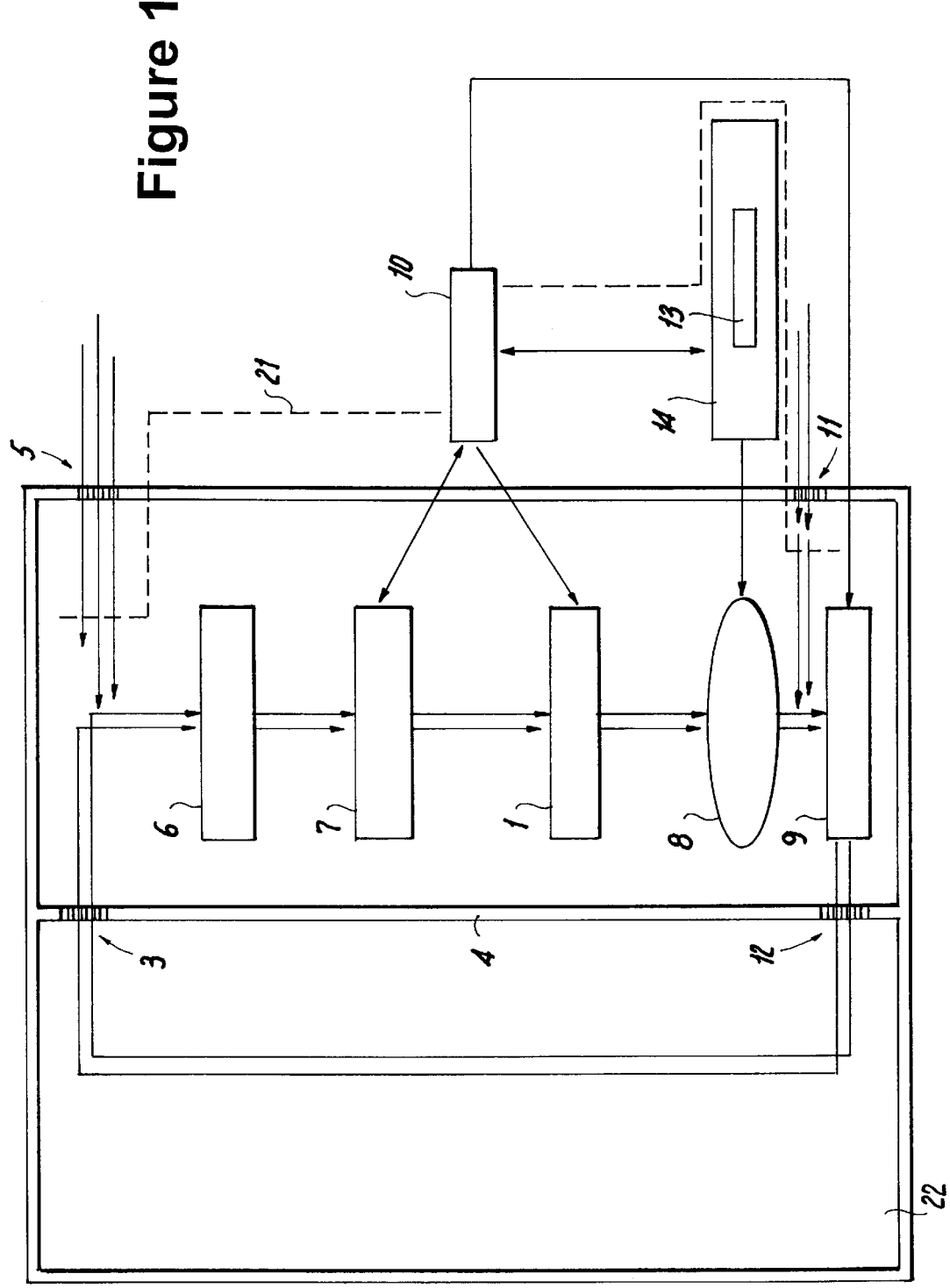
FIG. 1 is a conventional perspective view of an air conditioning compartment.
Figure 2:
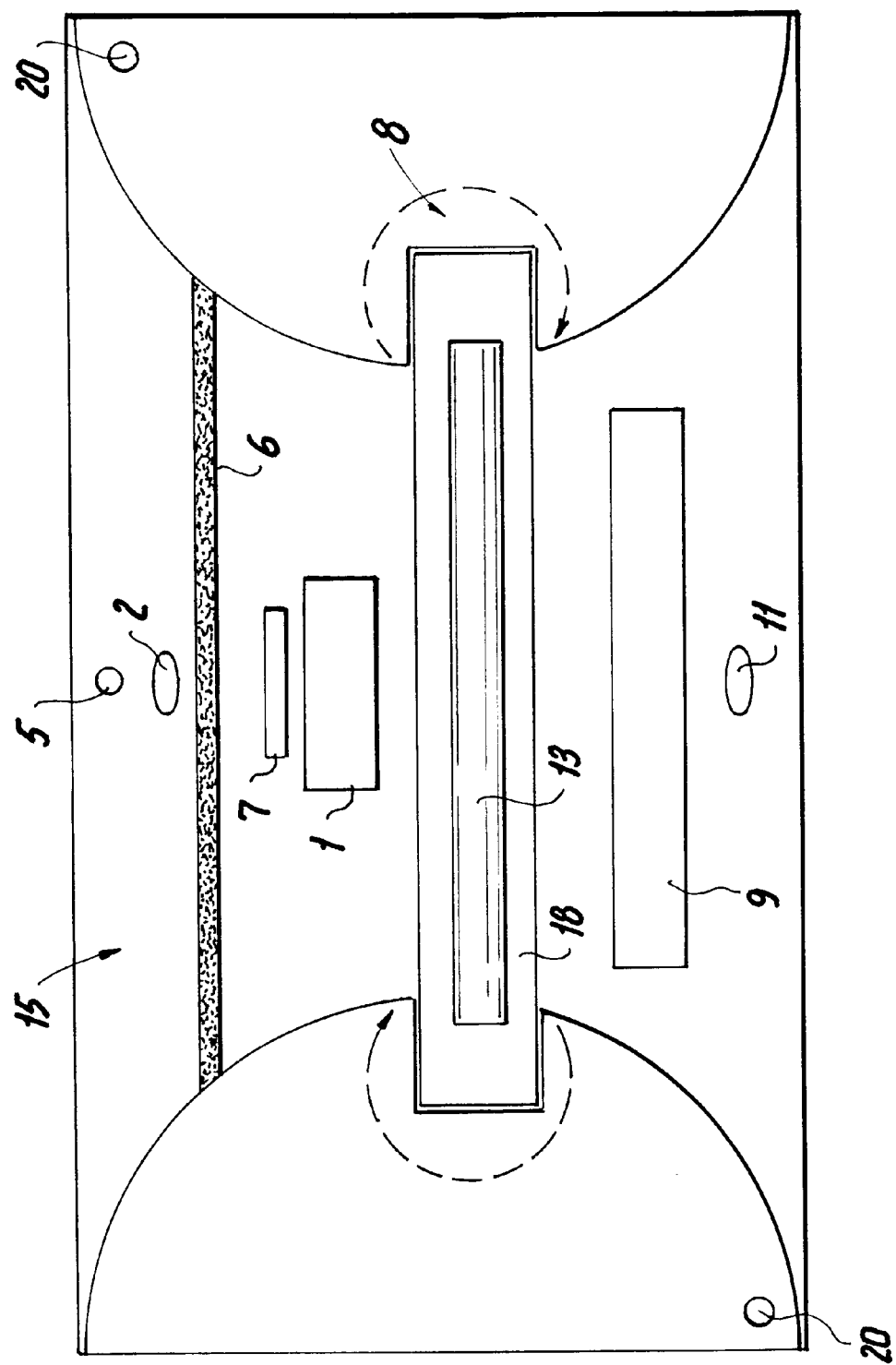
FIG. 2 is a conventional perspective view of the air conditioning compartment and the preferred makeup of the air sterilization system.

FIG. 1 schematically shows the flow of air through the air conditioning compartment and FIG. 2 shows a perspective of such compartment. The fan 1 sucks in fresh air from outside the incubator through the orifices 2 and circulating air through the orifices 3 of the tray 4, which separates the air conditioning compartment and the child's compartment (21 and 22). It can also take in medical oxygen supplied alternatively by the supplementary oxygen intake through orifice 5. The mixture of fresh air or oxygen and the circulating air passes through the air filter 6, the diverse temperature sensors 7, air flow and possibly other variables such as humidity and oxygen. The fan 1 pushes the filtered air towards the sterilization zone 8. The heater 9 heats the air that comes from the sterilization zone 8 in the appropriate quantity according to the temperature selected by the operator of the incubator in the controller 10, while humidity is added through the element 11 according to the requirements of such operator. The conditioned air mixture returns to the child's compartment through the orifices 12 of the tray 4. The operator can select the start or end of the sterilization action at any time by switching on or off respectively the air sterilization system. Similarly, the operator can select the desired values of the essential variables of the incubator, such as air temperature or that of the child, as well as other variables such as those already mentioned—oxygen and relative humidity—if the necessary accessories are available.

Figure 3A:
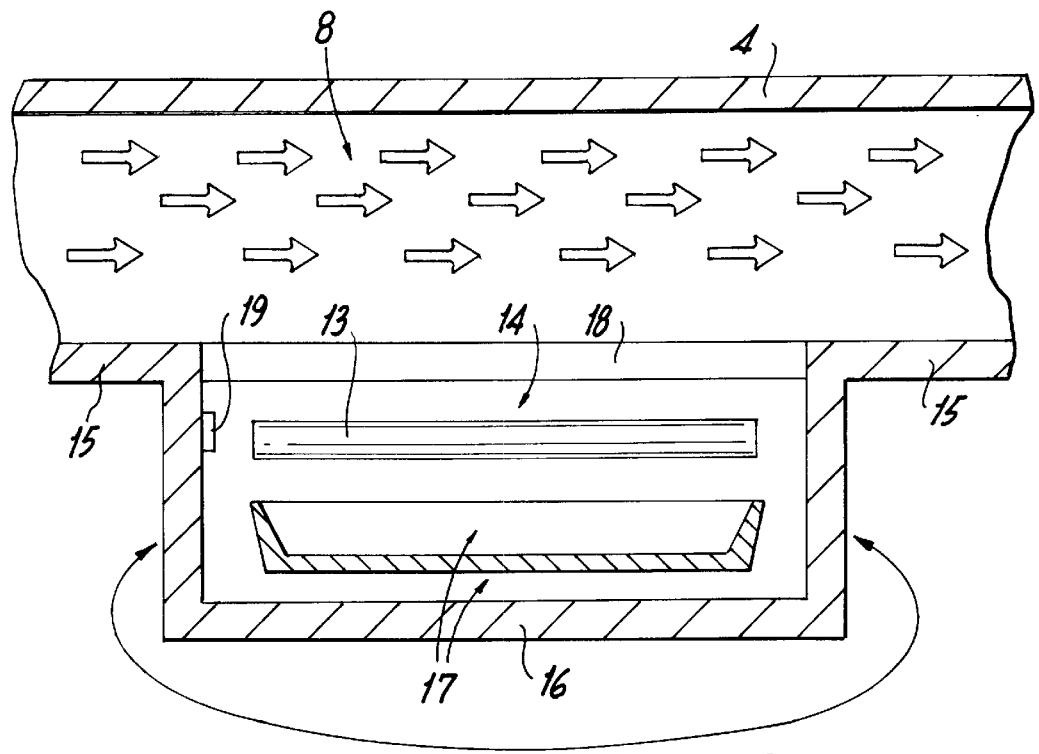
FIG. 3(a) is a cross-sectional view of the air conditioning compartment.
Figure 3B:
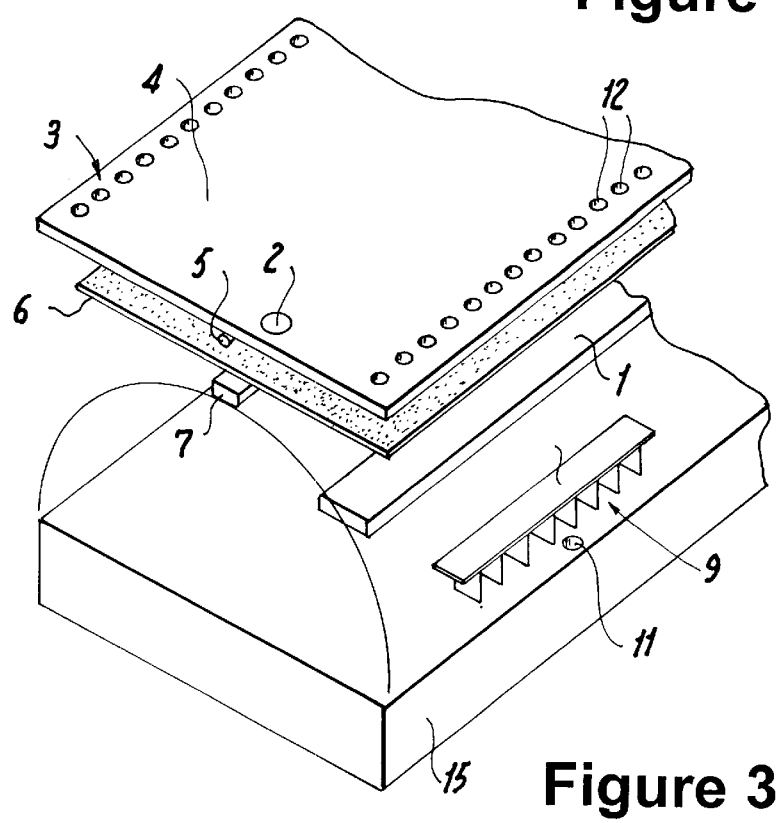
FIG. 3(b) is a conventional perspective view of the structure and shape of the preferred makeup of the incubator's air sterilization system.

FIGS. 3(a) and 3(b) show the preferred makeup of the air sterilization system in which a group of fluorescent lamps 13, of the type called germicide lamps, is arranged, which emit ultraviolet light of a wavelength that is predominantly around 253.7 nm of the electromagnetic spectrum. The range of the wavelengths with germicidal action in this part of the electromagnetic spectrum is from 200 to 300 nm, and consequently hereinafter this range of the electromagnetic spectrum is called the germicidal range. These lamps 13 are irradiating elements and are located in the irradiation chamber 14. In turn, such chamber 14 is located adjacent and built-in to the air distributor 1 of the air conditioning compartment 21 by its lower part, just below the aforementioned sterilization zone 8, and is confined by lateral and lower walls 16 of a material that reflects light in the germicidal range, avoiding an irradiation leak towards the outside of the incubator. That is, that the material used to form such walls 16 of the chamber 14 has as its physical properties, a high reflective nature and low transmittance particularly at the predominant wavelength of 253.7 nm and in general the germicidal range, as is aluminum. Also, the air distributor 15 and the tray 4 are made of materials with similar properties to avoid irradiation affecting persons near the incubator, including the child occupying it. Thus, by using low absorbency and low transmittance materials, the irradiation in the sterilization zone 8 is fully exploited. Sheets or particles of material with high absorbency in the germicidal range are only used in the areas near the orifices 2, 3, 5 and 12 of the air distributor 15 and the tray 4, to prevent the irradiation escaping by such orifices towards the child's compartment 22 or the outside of the incubator through the hood. The reflector 17 that is highly reflective in the germicidal range allows the greater part of the irradiation to be directed towards the sterilization zone 8, thereby increasing the irradiation in the volume of circulating air. The irradiation chamber 14 fits optically together with the air conditioning compartment by the coupling 14, made of a material (with high transmittance) that is translucent to the ultraviolet light of the aforementioned irradiation range of the germicidal lamps 13. The material used in the coupling 18 in the preferred makeup is made of Pyrex glass. Thus, the air that enters the air conditioning compartment 21 comes from the child's compartment 22, passes through the irradiated zone, thereby sterilizing the circulating air. The circulating air never comes into contact with the germicidal lamp 13, due to the fact that the irradiation chamber 14 is physically separated from the sterilization zone 8 by the coupling 18. The main functions of the coupling 18, besides allowing the passage of the irradiation, are to facilitate the cleaning of the incubator, since the cleaning staff do not normally have access to the interior of the irradiation chamber 14, and mainly that of sealing the same irradiation chamber 14 in case one or more of the lamps 13 break and release the mercury vapor they contain. In such case the incubator that is the object of this patent has a safety system in which the irradiation is measured by means of the optical sensor (photo-voltaic cell) 19 and it is determined whether the lamp or lamps 13 are emitting enough energy. The controller 10 activates the corresponding alarm to notify the personnel of inadequate functioning of the air sterilization system when the measured irradiation represents less than 80% of the expected irradiation with the lamps at 100% of their capacity, regardless of their accumulated functioning time. Thus, if the sterilization system has, for example, three lamps 13 and one breaks or stops functioning, the maximum combined capacity of the remaining ones is 66%, in which case the optical sensor 19 and the controller 10 activate the aforementioned alarm. Finally, the incubator includes a safety system for the operators, patients and other people near the equipment. This device consists of two electric switches 20 located at opposite corners of the air distributor 15 and electrically connected in series, so than they cut off the electric power supply to the lamps 13 when the tray 4 is lifted while the incubator is functioning.

Other alternative arrangements of the preferred air sterilization system based on the ultraviolet irradiation lamps are the three following: (1) the irradiating element is a voltaic arc lamp contained in a hermetic irradiation chamber, a coupling similar to the one used in the preferred makeup, and a subsystem for extracting or absorbing the gases given off by the voltaic arc electrodes; (2) the irradiating element is a magnetron that irradiates non-ionizing energy with frequencies around 915 MHz., known as microwaves; (3) the irradiating element is a collimating photonic reverberation system with a laser device whose wavelength is around 900 nm.

In this way a child incubator is obtained with an air sterilization system whose advantage over conventional incubators is the sterilization of the circulating air, thereby reducing the risk of cross infection and reducing the time the child stays in the incubator by providing it with healthier air and helping to control clinical or hospital infections.

We claim:

1. An air sterilization system for child incubators having a child compartment for receiving the child, an air conditioning compartment having an air filter for removing impurities, a fan for providing a flow of air to the system, a heater for temperature conditioning the flow of air, ducts for permitting inflow of air to the air conditioning compartment and the child compartment, comprising:

a non-ionizing radiation source located in the air sterilization system and adjacent the air conditioning system;

a tray arranged between the child compartment and the air conditioning compartment; said tray having orifices for receiving and transmitting the inflow of air between the air conditioning compartment and the child compartment;

a sterilization zone for sterilizing the flow of air; said sterilization zone being arranged between the tray and the non-ionizing radiation source;

sensors for monitoring physical variables within the system;

a heating element for heating the in flow of air passing through the sterilization zone;

a valve for regulating humidity of the in flow of air; and a controller for adjusting the sensors and the fan;

wherein the fan draws fresh air from outside into the incubator through the ducts, the fresh air flows from the incubator through orifices of the air conditioning compartment and into the air conditioning compartment, mixes with air which flows from the child compartment through the orifices of the tray to the air conditioning compartment and returns to the child compartment through other orifices of the tray, a mixture of fresh air and circulating air passes through the air filter and then passes through the sensors, the mixture of air passes through the fan, which forwards filtered air towards the sterilization zone, and through the heating element, which heats the filtered air to a temperature selected by an operator of the incubator, and wherein the filtered air is maintained within limits established by the controller, the humidity of the mixture of air is regulated by the valve, and conditioned and sterilized air is returned to the child compartment through the orifices of the tray.

2. An air sterilization system for child incubators, according to claim 1, further comprising:

a reflector for directing irradiation from the non-ionizing radiation source towards the sterilization zone to increase irradiation in the circulating air.

3. An air sterilization system for child incubators according to claim 1, further comprising:
   a coupling; said coupling permitting arrangement of the sterilization chamber and the air conditioning compartment such that air in the air conditioning compartment can be easily and safely cleaned;
   wherein the sterilization chamber is sealable to prevent unwanted releases of polluting vapors emanating from the non-ionizing radiation source.

4. An air sterilization system for child incubators according to claim 1, wherein the controller emits an audible and visible alarm when one of a failure occurs in the non-ionizing radiation source, an efficacy and an efficiency of the non-ionizing radiation source is reduced.

5. An air sterilization system for child incubators according to claim 1, further comprising:
   walls arranged around the sterilization chamber; said walls being made of a material that reflects light in a germicidal range wavelength;
   wherein the walls prevent outward leaks of irradiation from the incubator, the walls have a high reflectance level and a low transmittance level to a wavelength in a range of from 253.7 nm to the germicidal range wavelength.

6. An air sterilization system for child incubators according to claim 5, wherein the walls are aluminum.

7. An air sterilization system for child incubators according to claim 5, wherein the ducts are aluminum.

8. An air sterilization system for child incubators according to claim 1, wherein the non-ionizing radiation source comprises at least one germicidal fluorescent lamp which emits ultraviolet light having a wavelength of approximately 253.7 nm, and
   wherein a range of ultraviolet wavelength having germicidal action is from 200 to 300 nm.

9. An air sterilization system for child incubators according to claim 6, wherein the ultraviolet wavelengths having germicidal action is a germicidal range wavelength.

10. An air sterilization system for child incubators according to claim 6, wherein the at least one germicidal fluorescent lamp is located in an irradiation chamber.

11. An air sterilization system for child incubators according to claim 1, further comprising:
   a switch device for disabling the non-ionizing radiation source when one of the air conditioning compartment and the sterilization chamber is exposed to atmosphere to avoid irradiating people located near the incubator.

* * * * *